United States Patent [19]

Long et al.

[11] Patent Number: 5,054,328
[45] Date of Patent: Oct. 8, 1991

[54] GAS ANALYZER WITH DIFFUSION FILTER

[75] Inventors: Stephen E. Long, Murrysville; Albert A. Poli, Pittsburgh, both of Pa.

[73] Assignee: Mine Safety Appliances Company, Pittsburgh, Pa.

[21] Appl. No.: 430,377

[22] Filed: Nov. 2, 1989

[51] Int. Cl.$^5$ ............................................. G01N 1/22
[52] U.S. Cl. .................. 73/864.81; 73/31.07; 73/863.23
[58] Field of Search ........... 73/863.23, 863.24, 863.25, 73/864.81–864.87, 31.07

[56] References Cited

U.S. PATENT DOCUMENTS

| | | | |
|---|---|---|---|
| 3,367,850 | 2/1968 | Johnson | 73/863.23 X |
| 3,431,771 | 3/1969 | Tsien | 73/31.07 X |
| 3,457,787 | 7/1969 | Maatsch et al. | 73/863.24 X |
| 3,552,211 | 1/1971 | Dollinger et al. | 73/863.24 X |
| 3,718,434 | 2/1973 | Pierce | 73/31.07 X |
| 3,926,561 | 12/1975 | Lucero | 73/23.35 X |
| 3,942,357 | 3/1976 | Jenkin | 73/31.07 |
| 3,955,943 | 5/1976 | Pontius | 55/16 |
| 4,656,865 | 4/1987 | Callan | 73/38 |

FOREIGN PATENT DOCUMENTS 142439 8/1984 Japan .

OTHER PUBLICATIONS

*Patent Abstracts of Japan* (59-142439); GRP; p. 321, vol. 8, No. 275; ABS Pub. Date 12/15/1984.

*Primary Examiner*—Tom Noland

[57] ABSTRACT

A gas analyzer comprises a diffusion filter to segregate sampled gases containing liquid and particulate solid contaminants from the analyzer. A gas permeable diffusion membrane separates a flowing stream of dirty sample gas from a closed circuit clean gas stream circulated through an analyzer. The membrane does not pass liquids or particulate solids but does permit rapid diffusion of gases so the gas composition in the closed circuit rapidly reaches equilibrium with the sample gas.

4 Claims, 1 Drawing Sheet

GAS ANALYZER WITH DIFFUSION FILTER

FIELD OF THE INVENTION

This invention relates to gas analyzers and more particularly to analyzers having filters to separate liquids and particulate solids from the gas to be analyzed.

BACKGROUND OF THE INVENTION

Most gas sensors and analyzers, e.g. electrochemical, catalytic combustion, semiconductor, infrared, ultraviolet, flame ionization, gas chromatographs and mass spectrophotometers, are adversely affected by water and particulate solids. It is conventional practice to flow such dirty gas streams through water traps and/or filters, usually paper or fritted glass or metal filters, to provide a clean gas stream to the analyzer. Many gas streams have condensable liquids that together with entrained particulate matter form a solid sludge that plugs filters. Examples of particularly difficult sample streams are stack analysis for combustion control and incinerator exhaust analysis. In these cases, both condensables and particulates exist, and frequently dissolved corrosive gases, such as $SO_3$ and $HCl$. Conventional filtering techniques suffer from entrainment of contaminants or plugging of filter media. Even filters using permeation driers, inertial filtering, water wash and other methods, have proven to require very frequent maintenance and are marginal at best.

BRIEF DESCRIPTION OF THE INVENTION

In accordance with this invention a gas permeable diffusion membrane separates a flowing stream of dirty sample gas from a closed circuit clean gas stream circulated through an analyzer. The dirty and clean streams are preferably flowed in opposite directions along the diffusion membrane. The membrane does not pass liquids or particulate solids but does permit rapid diffusion of gases so the gas composition in the closed circuit rapidly reaches equilibrium with the sample gas.

The membrane is preferably a synthetic, gas porous material that does not readily wet, to minimize clogging. Preferred membranes are preferably Zitex ® or Goretex ® porous fluorocarbon membranes. Other membrane materials may be used provided they have characteristics similar to Zitex and Goretex, including not becoming wet by water or other liquid in the sample gas, having a large number of pores (e.g. 50% porous) which in turn are of small pore size and being thin enough to permit a sufficiently fast gas diffusion rate that gives a substantial equilibrium between the sample and closed circuit gas streams.

DETAILED DESCRIPTION OF THE PREFERRED EMBODIMENT

Figure 1:
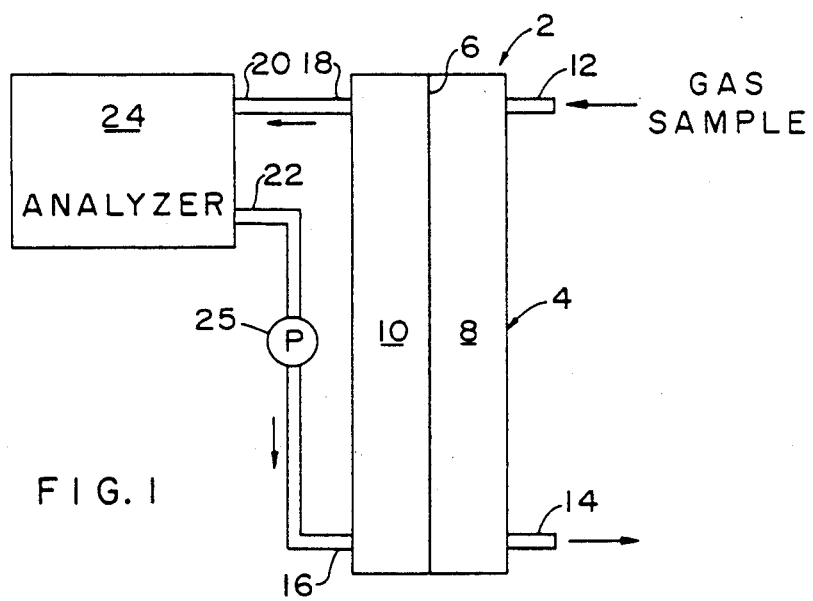
FIG. 1 is a schematic diagram of the gas analyzers with the diffusion filter of this invention.

With reference to FIG. 1, a diffusion filter 2 comprises a housing 4, having a chamber divided by membrane into a first elongate compartment 8 and a second elongate compartment 10. The first compartment has a sample gas inlet 12 and a sample gas outlet 14, so that sample gas can be flowed lengthwise through the compartment. Compartment 10 likewise has an inlet 16 and an outlet 18 connected in a closed circuit loop with the inlet 20 and outlet 22 of an analyzer 24. Pump 25, or a pump incorporated in the analyzer, circulates gas in the closed circuit.

In operation, fluid or particulate solids in the sample stream are prevented by the membrane from passing from compartment 8 into compartment 10, and are discharged with the gas stream from outlet 14. Gas from compartments 8 and 10, however, are free to diffuse through the membrane, so the composition of gas in the closed circuit is in equilibrium with and substantially the same composition as the gas phase of the sample stream. The area and thickness of the membrane are selected to provide a diffusion rate sufficient to give a desired response time to reach equilibrium.

Exemplary of the invention, using a wet sample stream of $CO_2$ in air and a Goretex No. S10755 (expanded PTFE; thickness, 0.010 inches; density, 0.7 g/cc; porosity, 68%) membrane having 4.5 square inches of surface exposed to the sample and analytical gas streams, the interposition of the diffusion filter between a $CO_2$ electrochemical analyzer and the sample stream increased response time less than 5%.

Figure 2:
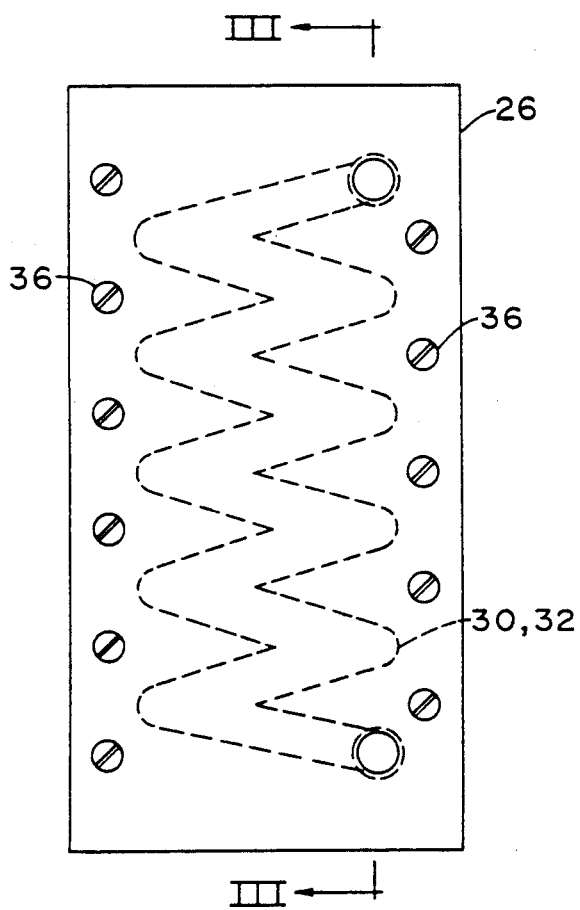
FIG. 2 is an elevation of the diffusion filter of FIG. 1.
Figure 3:
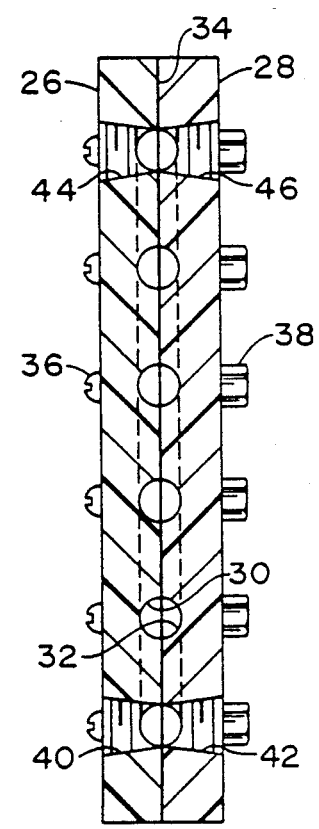
FIG. 3 is a section on line III—III of FIG. 2.

FIGS. 2 and 3 show the now preferred embodiment of the diffusion filter in more detail.

Housing blocks 26 and 28 have matching serpentine semicircular grooves 30 and 32 respectively. A diffusion membrane 34 is secured between the housing blocks by bolts 36 and nuts 38. The grooves 30 and 32 form two compartments separated by the membrane 34. Inlet and outlet connections to each compartment are provided by bores 40, 42, 44 and 46. This construction provides a long flow path with good mechanical support of the membrane.

It is understood that this invention may be practiced otherwise than as described above within the scope of the appended claim.

We claim:

1. A gas analyzer comprising a housing forming a chamber, a gas permeable membrane dividing the chamber into a first and a second compartment, each compartment having an inlet and an outlet, means to introduce a sample stream comprising a gas phase to the first compartment inlet, the gas analyzer having an inlet and outlet, means to fluidically connect the analyzer inlet and the second compartment outlet, means to connect the analyzer outlet and the second compartment inlet, and means to circulate gas to be measured through the analyzer and second compartment, in a closed circuit said membrane being sufficiently gas permeable that the said gas to be measured is substantially the same composition as the sample stream gas phase.

2. A gas analyzer according to claim 1 in which the membrane is polytetrafluoroethylene.

3. A gas analyzer according to claim 1 or 2 in which the first and second compartments are vertically oriented elongate compartments, the first compartment inlet being near the top and the first compartment outlet being near the bottom of the first compartment, the second compartment inlet being near the bottom and the outlet near the top of the second compartment.

4. A method of removing liquid and particulates from an analytical sample having a gas phase comprising flowing the sample through a first chamber having a gas permeable membrane wall, circulating gas in a closed circuit through an analyzer and a second chamber having a common gas permeable wall with the first chamber, said wall being sufficiently gas permeable that the said circulating gas is substantially the same composition as the sample gas phase.

* * * * *